US010456270B2

(12) United States Patent
Slater

(10) Patent No.: US 10,456,270 B2
(45) Date of Patent: Oct. 29, 2019

(54) ANTERIOR HIP EXTRACTOR

(71) Applicant: Shukla Medical, Piscataway, NJ (US)

(72) Inventor: Stephen M. Slater, Morris Plains, NJ (US)

(73) Assignee: Shukla Medical, St. Petersburg, FL (US)

( * ) Notice: Subject to any disclaimer, the term of this patent is extended or adjusted under 35 U.S.C. 154(b) by 274 days.

(21) Appl. No.: 15/675,166

(22) Filed: Aug. 11, 2017

(65) Prior Publication Data

US 2018/0042734 A1 Feb. 15, 2018

Related U.S. Application Data

(60) Provisional application No. 62/374,422, filed on Aug. 12, 2016.

(51) Int. Cl.
*A61F 2/46* (2006.01)
(52) U.S. Cl.
CPC .......... *A61F 2/4607* (2013.01); *A61F 2/4603* (2013.01); *A61F 2002/4619* (2013.01); *A61F 2002/4629* (2013.01); *A61F 2002/4681* (2013.01)

(58) Field of Classification Search
CPC .................. A61F 2/4607; A61F 2/4603; A61F 2002/4629; A61F 2002/4619
See application file for complete search history.

(56) References Cited

U.S. PATENT DOCUMENTS

| | | | | | |
|---|---|---|---|---|---|
| 3,801,989 | A | * | 4/1974 | McKee | A61F 2/32 623/22.12 |
| 3,857,389 | A | * | 12/1974 | Amstutz | A61F 2/4607 606/86 R |
| 4,222,382 | A | * | 9/1980 | Antonsson | A61F 2/4607 606/100 |

* cited by examiner

*Primary Examiner* — Christian A Sevilla
(74) *Attorney, Agent, or Firm* — Kim IP Law Group

(57) ABSTRACT

An implant extraction device and method are provided that are designed for the direct anterior approach method of hip implant removal. The device includes a proximal end having a first aperture for receiving the neck of a femoral implant, and a second aperture through which a clamp shaft is delivered on an axis approximately perpendicular to the longitudinal axis of the first aperture. An arcuate column extends from the proximal end. The shape of the arcuate column effectively orients the extraction device and an attachable impaction frame relative to one another such that the force applied to the frame to remove the implant is essentially parallel to the longitudinal axis of the hip implant, thus minimizing the likelihood of damage to the femur bone caused by excessive or unbalanced forces.

17 Claims, 6 Drawing Sheets

ANTERIOR HIP EXTRACTOR

CROSS-REFERENCE TO RELATED APPLICATIONS

This application claims the benefit of U.S. Provisional Application No. 62/374,422, filed Aug. 12, 2016, the entire disclosure of which is incorporated by reference herein in its entirety.

BACKGROUND OF THE INVENTION

The exemplary embodiments of the subject disclosure relate generally to the field of medical device implant extraction tools. In particular, the subject disclosure relates to a hip implant extraction tool.

Hip replacement implants are used to replace the hip joints in individuals who suffer from bone degeneration or hip injuries that damage and disable the joint. Occasionally, the implants in some patients will need to be removed or replaced.

Hip implant removal is typically performed using a posterior approach, and many surgical tools and techniques have been developed for this approach. However, the posterior approach is not always the best approach, and other techniques have been developed. The direct anterior approach (DAA) method is another technique used by surgeons for both primary and revision hip replacement surgeries. The incision site for DAA is positioned towards the front of the patient in contrast to the more widely used posterior approach.

However, conventional medical devices and surgical tools are not yet capable of allowing for proper execution of a DAA. As such, surgeons typically use equipment designed for the posterior approach when performing a DAA. This can be problematic, e.g., a hip implant extractor designed for a posterior approach may cause excess stress or unintended damage to the bone.

Therefore, there is still a need in the art for an extraction tool that can attach to an implant during a DAA so that the implant may be readily removed from the femur with improved efficiency and minimal stress upon the bone.

BRIEF SUMMARY

The present exemplary embodiments provide an implant extractor that attaches to an implant such that the force used to remove the implant aligns with the femur, thereby resulting in minimal stresses to the bone.

In accordance with an exemplary embodiment of the subject disclosure, there is provided an implant extraction device that includes an arcuate frame. The arcuate frame includes a proximal end having a first aperture for receiving an implant, and a second aperture adjacent the first aperture for receiving a fastener. The arcuate frame also includes a distal end having a recess for receiving an adapter.

In an aspect of the exemplary embodiment, the second aperture is in fluid communication with the first aperture. The first aperture has a longitudinal axis that is oriented about 40 to 50 degrees relative to a longitudinal axis of the recess. The distal end of the arcuate frame includes a linear portion.

In accordance with another exemplary embodiment of the subject disclosure, there is provided an anterior hip extractor comprising a base and an arm. The base includes an aperture for receiving a hip implant, and a fastener for fastening the hip implant received within the aperture. The arm arcuately extends from the base.

In an aspect of the exemplary embodiment, the arm includes an arcuate portion having an arc length of about 40 to 60 degrees. The arm further includes a linear portion extending from the arcuate portion. The linear portion of the arm has a longitudinal axis that is oriented about 40 to 50 degrees relative to a longitudinal axis of the aperture. The base includes a cavity for receiving the fastener. The cavity is in fluid communication with the aperture.

In another aspect of the exemplary embodiment, the fastener includes a screw and a clamp shaft. The clamp shaft includes a plastic bushing. The clamp shaft further includes a rounded end having a plurality of ribs. The anterior hip extractor further includes an adapter attachable to the arm for attaching to a secondary extraction device. The adapter is a substantially cylindrical shaft having threaded proximal and distal ends. Additionally, the adapter is threadedly engaged with the arm.

In accordance with another exemplary embodiment of the subject disclosure, there is provided an anterior hip extractor comprising a base and an arm. The base includes an aperture for receiving an implant, and a fastener for fastening the implant received within the aperture. The arm extends from the base and includes a terminal end extending in a direction oriented about 40 to 50 degrees relative to a longitudinal axis of the base.

In an aspect of the exemplary embodiment, the base includes a cavity in fluid communication with the aperture for receiving the fastener. The arm arcuately extends from the base. Additionally, the fastener applies a securing force to the implant in a direction transverse to a longitudinal axis of the aperture.

In accordance with another exemplary embodiment of the subject disclosure, there is provided a method of extracting a hip implant from a bone. The method includes the steps of attaching an anterior hip extractor to the hip implant, orienting the terminal end of the arm to be substantially parallel with a longitudinal axis of a stem of the hip implant, and applying a force to the anterior hip extractor along an axis substantially parallel to the longitudinal axis of the stem of the hip implant.

In accordance with another exemplary embodiment of the subject disclosure, there is provided a method of extracting a hip implant from a bone. The method includes the steps of attaching an extractor to the implant, aligning the implant extractor to the implant, attaching an impaction frame to the extractor, and applying a force to the impaction frame to remove the implant.

In an aspect of the exemplary embodiment, the extractor attaches to a neck of the implant. In another aspect, the extractor is shaped such that when an impaction frame is attached to the extractor, the frame is positioned away from the patient's body. In yet another aspect, the extractor is shaped to allow attachment of the frame to the distal section of the extractor, with the frame having a striking surface aligned such that the force used to extract the implant is essentially parallel to the femur. In another aspect, the extractor is shaped such that an impaction surface of the frame is essentially perpendicular to the femur when the frame is mounted on the extractor, causing the force applied to the frame to be essentially parallel to the femur.

In accordance with the exemplary embodiments of the subject disclosure, the direct anterior approach (DAA) is a technique used by surgeons for both primary and revision hip replacement surgeries. The incision site for DAA is positioned towards the front of the patient when compared to the more widely used posterior approach. An anterior hip extractor of the subject disclosure is designed so that it can be attached to the hip implant and has the ability to be used with other conventional extraction tools to easily remove the implant from the patient using the DAA.

Other features and advantages of the subject disclosure will be apparent from the following more detailed description of the exemplary embodiments, taken in conjunction with the accompanying drawings which illustrate, by way of example, the principles of the subject disclosure.

BRIEF DESCRIPTION OF THE SEVERAL VIEWS OF THE DRAWINGS

The foregoing summary, as well as the following detailed description of the exemplary embodiments of the subject disclosure, will be better understood when read in conjunction with the appended drawings. For the purpose of illustrating the subject disclosure, there are shown in the drawings exemplary embodiments. It should be understood, however, that the invention is not limited to the precise arrangements and instrumentalities shown.

In the drawings.

DETAILED DESCRIPTION OF THE INVENTION

Figure 1:
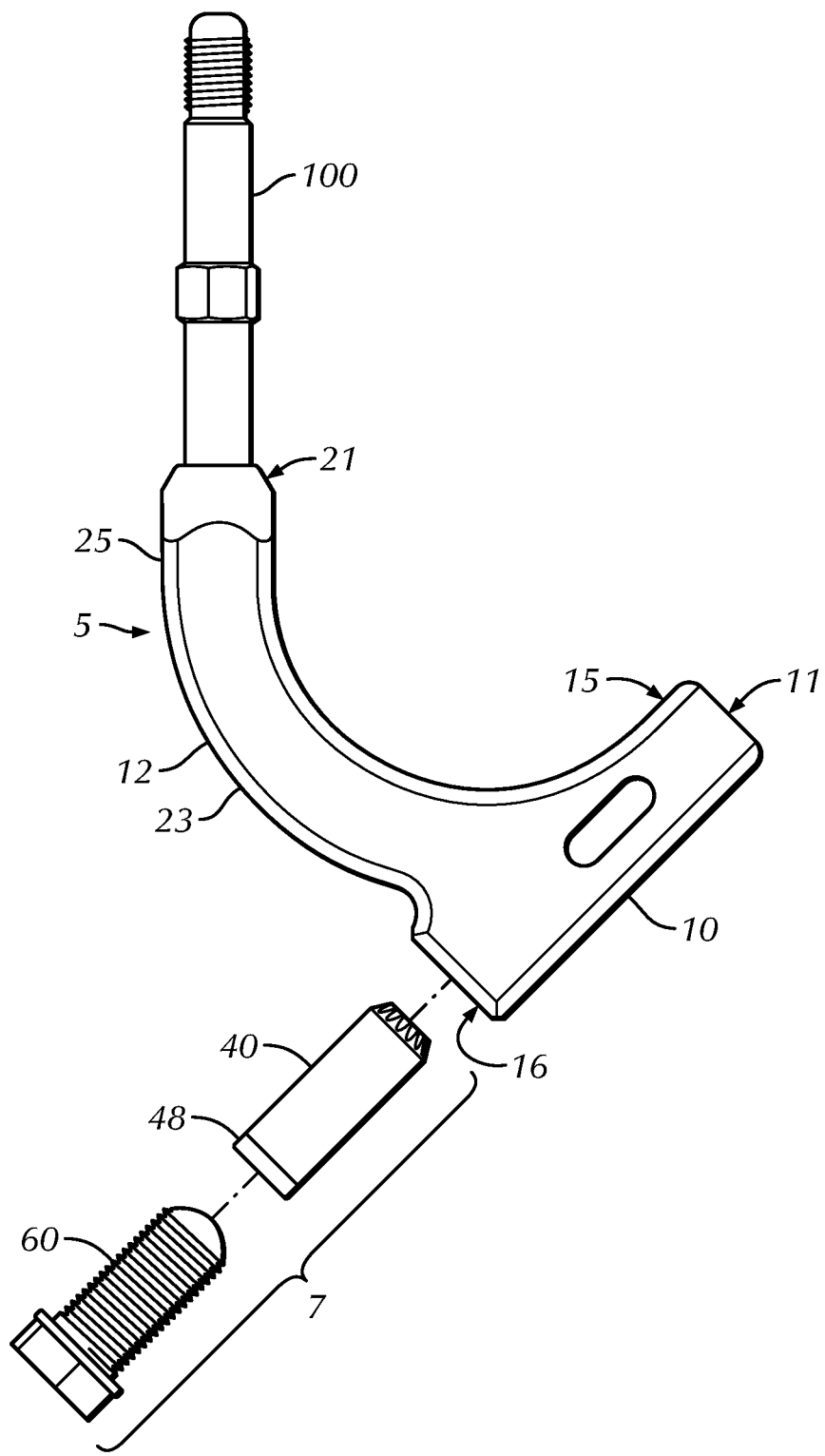
FIG. 1 is a side view of an implant extraction device in accordance with an exemplary embodiment of the subject disclosure.

Reference will now be made in detail to the various exemplary embodiments of the subject disclosure illustrated in the accompanying drawings. Wherever possible, the same or like reference numbers will be used throughout the drawings to refer to the same or like features. It should be noted that the drawings are in simplified form and are not drawn to precise scale. Certain terminology is used in the following description for convenience only and is not limiting. Directional terms such as top, bottom, left, right, above, below and diagonal, are used with respect to the accompanying drawings. The term "distal" shall mean away from the center of a body. The term "proximal" shall mean closer towards the center of a body and/or away from the "distal" end. The words "inwardly" and "outwardly" refer to directions toward and away from, respectively, the geometric center of the identified element and designated parts thereof. Such directional terms used in conjunction with the following description of the drawings should not be construed to limit the scope of the subject disclosure in any matter not explicitly set forth. Additionally, the term "a," as used in the specification, means "at least one." The terminology includes the words above specifically mentioned, derivatives thereof, and words of similar import.

References to proximal elements described herein refer to being closer to the femur or femur implant or further from the surgeon, while references to distal elements refer to being further from the femur or femur implant or closer to the surgeon. References to the geometric orientation of the elements of the exemplary embodiments with respect to the patient, femur or surgeon are approximate, with appropriate adjustment of the extractor and frame understood to be available to the surgeon depending on the needs of the surgery or patient.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the subject disclosure can be presented in a range format. It should be understood that the description in range format is merely for convenience and brevity and should not be construed as an inflexible limitation on the scope of the exemplary embodiments. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, and 6. This applies regardless of the breadth of the range.

Furthermore, the described features, advantages and characteristics of the exemplary embodiments of the subject disclosure may be combined in any suitable manner in one or more embodiments. One skilled in the relevant art will recognize, in light of the description herein, that the exemplary embodiments can be practiced without one or more of the specific features or advantages of a particular embodiment. In other instances, additional features and advantages may be recognized in certain embodiments that may not be present in all exemplary embodiments of the subject disclosure.

Referring now to the drawings, wherein aspects of the subject disclosure are shown, FIGS. 1-6 illustrate an implant extraction device 5 in accordance with an exemplary embodiment. For exemplary purposes only, the implant extraction device 5 is illustrated as an anterior hip extractor.

Figure 2:
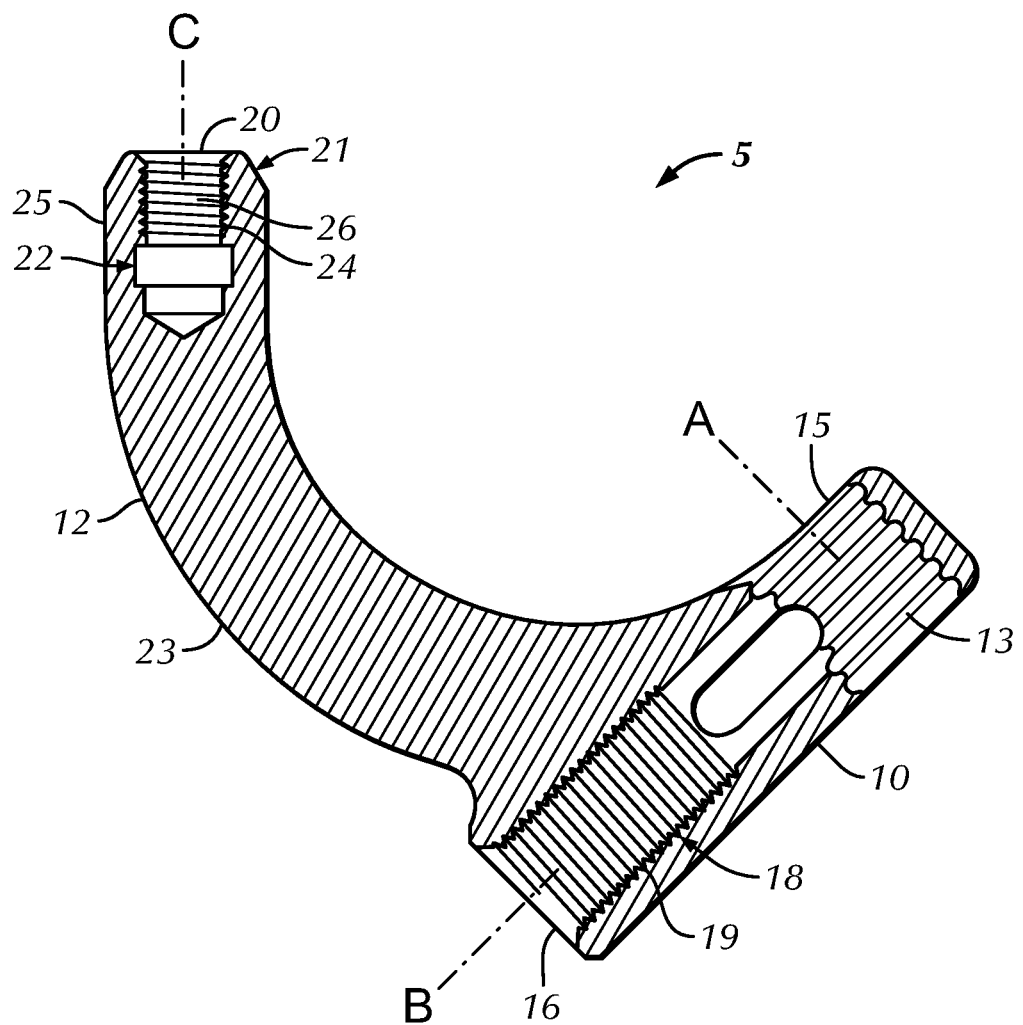
FIG. 2 is a cross-sectional view of the implant extraction device of FIG. 1.

Referring now to FIGS. 1 and 2, the anterior hip extractor 5 includes a base 10 and an arm 12 extending from the base. Alternatively expressed, the base 10 and arm 12 form an arcuate frame. In accordance with an aspect of the present embodiment, the arm 12 arcuately extends from the base. The implant extraction device 5 includes a proximal end 11 integral to the base 10, and a distal end 21 integral to the arm 12.

In accordance with an exemplary embodiment, the base 10 includes a first aperture 15, a second aperture 16 and a fastener 7. The first aperture 15 is positioned adjacent the proximal end of the base and configured to receive a neck of or a portion of a femoral implant 1000. Preferably, the first aperture 15 is a cylindrical aperture defining a longitudinal axis A. The first aperture can optionally include ribs 13 about its inner surface for engaging with the femoral implant.

FIG. 2 shows a cross-section of the implant extraction device 5. On the proximal end 11 of base 10, the first aperture 15 is shown with the ribs or ridges 13 along its interior wall. These ridges engage the neck of the implant when the neck is placed into aperture 15 and engaged by the fastener 7, e.g., by contact with a clamp shaft 40 of the fastener.

The second aperture 16 is positioned adjacent the first aperture 15 and configured to receive the fastener 7. In an exemplary embodiment, the fastener 7 includes the clamp shaft 40 and a screw 60. The fastener 7 fastens the femoral or hip implant received within the first aperture 15 to the implant extraction device. The second aperture 16 of the base 10 defines a cavity 18 for receiving the fastener 7. Preferably, the cavity 18 is configured to have a longitudinal axis B substantially perpendicular to the longitudinal axis A of the first aperture. In accordance with an aspect, the second aperture 16 is configured to have female cylindrical threads 19 for engaging with the screw 60. It is to be appreciated that the screw 60 can be securely held in place inside the cavity 18 in a number of ways including, but not limited to, screw threads, hooks, clasps, grooves, rivets and so forth.

In an aspect, the aperture 15 is in fluid communication with the second aperture 16. In other words, the cavity 18 is in fluid communication with aperture 15.

The implant extraction device can optionally include an adapter 100 for attachment with the distal end 21 of the arm 12. In this configuration, the distal end of the arm 12 includes a recess 20 for receiving the adapter 100. The adapter 100 enables attachment of a secondary extraction device, such as an impaction frame (not shown), to the implant extraction device 5.

Figure 5:
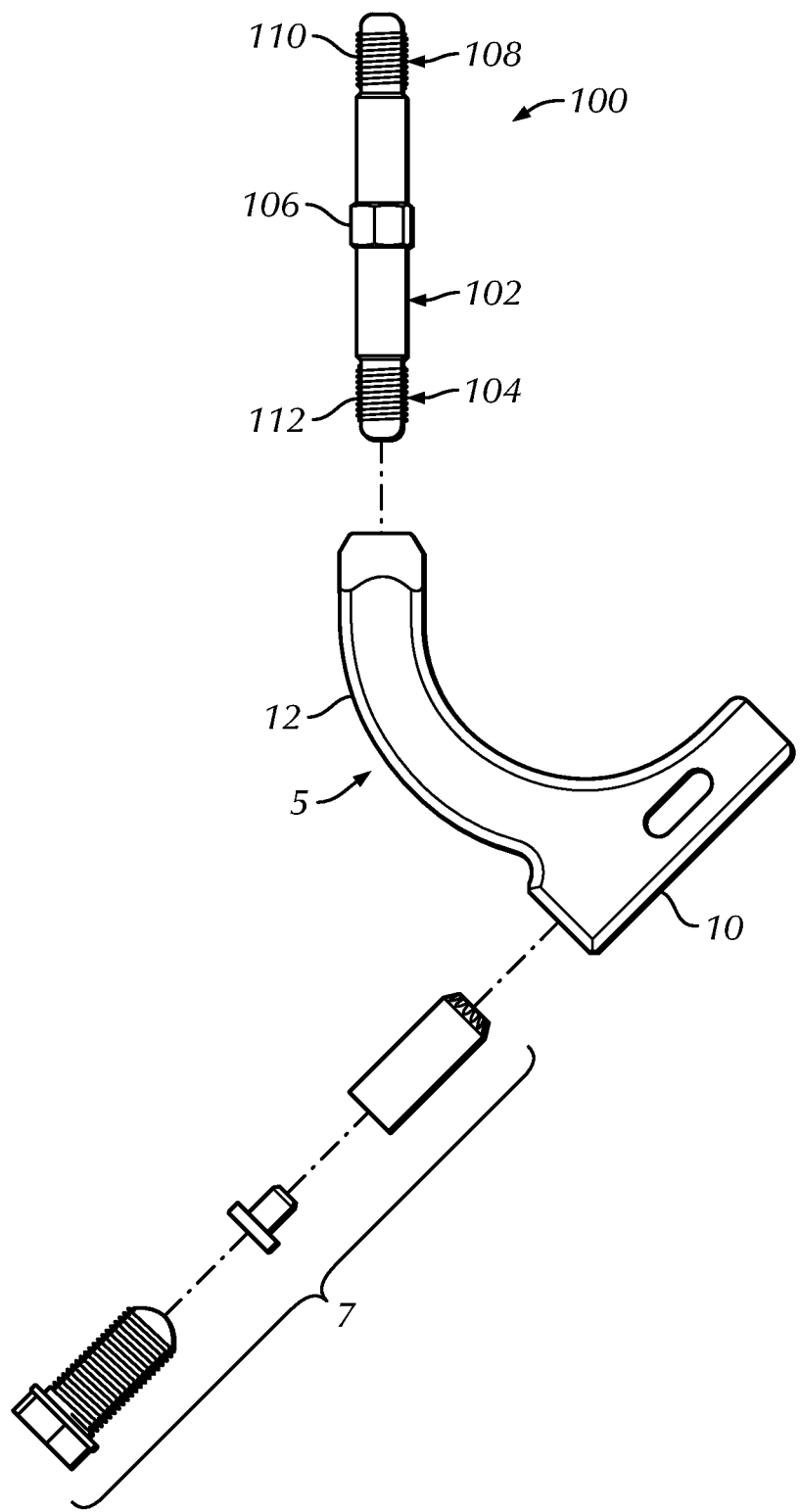
FIG. 5 is an exploded side view of the implant extraction device of FIG. 1.

In accordance with an exemplary embodiment, the adapter is configured as shown in FIG. 5. The adapter 100 includes a cylindrical shaft 102 having a proximal shaft end 104, a hexagonal section 106, and a distal shaft end 108. The proximal shaft end 104 includes first adapter threads 112. In an aspect, the adapter 100 is threadedly engaged with the arm 12 via the first adapter threads 112. The hexagonal section 106 is configured so that it may be turned by hand or by tool e.g., to assemble to the extraction device or to mount the secondary extraction device, commonly an impaction frame (not shown), on the distal shaft end 108. Preferably, the hexagonal section 106 is proportioned to fit into a standard chuck or handle rotationally and axially. The distal shaft end 108 has second adapter threads 110 to enable attachment to e.g., an impaction frame (not shown). For example, an impaction frame applicable to the exemplary embodiment includes the C-Frame sold by Shukla Medical of Piscataway, N.J. It is to be appreciated that the adapter 100 can be securely held in place to the arm in a number of ways including, but not limited to, screws, hooks, clasps, grooves, rivets and so forth.

As best shown in FIG. 5, the cylindrical shaft 102 is generally a cylindrical member having a longitudinal central axis and a circular cross-section. However, the cylindrical shaft 102 can have any shaped cross-section such as hexagonal, polygonal or any other shape suitable for its intended purpose. The cylindrical shaft 102 can also be formed with a plurality of shaft segments having different cross-sectional diameters. Generally, the cylindrical shaft 102 is illustrated as straight, although it may have a lordotic curve or be otherwise bent or curved. The cylindrical shaft 102 may have any desired length sufficient for its intended purpose.

Figure 6:
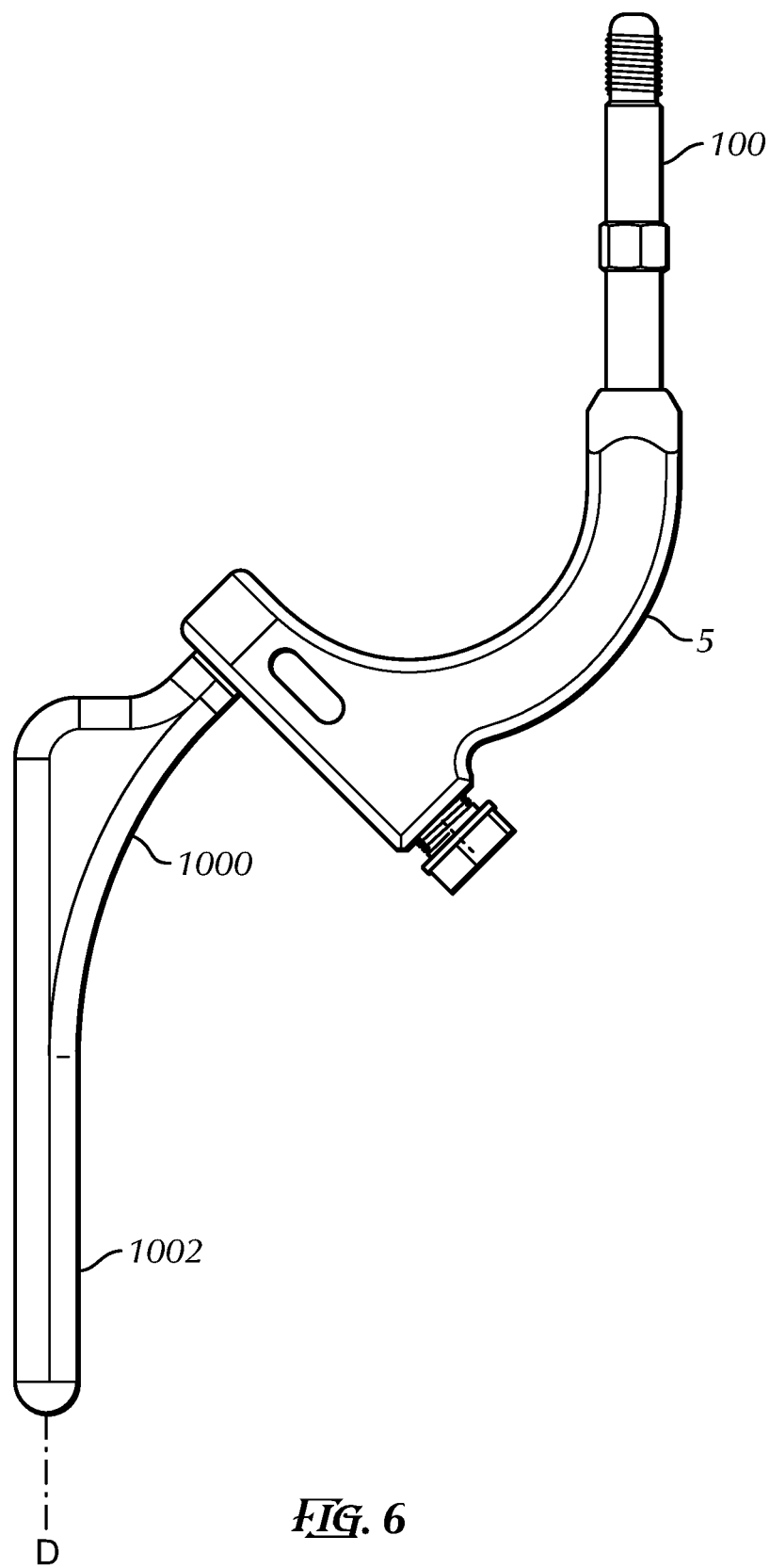
FIG. 6 is a side view of the implant extraction device of FIG. 1 attached to a hip implant.

In use, an impaction frame is attached to distal shaft end 108 by engaging a threaded aperture on the impaction frame. Alternative attachment structures may also be used, including spring-loaded indent pins, clamping mechanisms, attachment screws, or the like, as long as the impaction frame may be firmly but removably mounted to the adapter 100. The entire structure may be manipulated to align a force supplied by application of the impaction hammer with a longitudinal axis of the femur implant e.g., a longitudinal axis of a hip implant stem. That is, the striking surface of the impaction frame is perpendicular to the longitudinal axis of the femur, and the force delivered to the striking surface would be delivered in a vector parallel to the longitudinal axis of the implant and/or the femur bone. FIG. 6 illustrates attachment of the implant extraction device 5 to a femoral implant with the arm terminating in a direction parallel with a longitudinal axis of a hip implant stem 1000.

In accordance with an aspect of the exemplary embodiment, the arm 12 is configured as an arcuate column so that in use, when a secondary extraction device such as an impaction frame is attached to the adapter 100, an impaction surface of the impaction frame is approximately perpendicular to the longitudinal axis of the femoral implant and the force delivered to the impaction frame would be applied in a direction approximately parallel to a longitudinal axis of the femoral implant and consequently the femur bone.

In accordance with an exemplary embodiment illustrated in FIGS. 1 and 2, the arm 12 includes an arcuate portion 23 having an arc length of about 40 to 60 degrees, about 45 to 55 degrees, or about 45 to 50 degrees. It is understood that although the arm 12 is illustrated as an arcuate column, a plurality of connected members or pivotably hinged members (with a locking mechanism) or other shapes that can effectively orient the extractor as needed are also alternative exemplary embodiments for the arm 12, and reference to an arcuate shape refers to all of these exemplary embodiments.

Further, as shown e.g., in FIGS. 2 and 6, the arm 12 extends from the base 10 and includes a terminal end extending in a direction that is oriented about 40 to 50 degrees, about 40 to 45 degrees, or about 45 to 50 degrees, relative to the longitudinal axis B of the base 10.

Additionally, in accordance with another exemplary embodiment, the arm 12 further includes an angular member i.e., a linear portion 25 extending from the arcuate portion 23 about its distal end. A longitudinal axis C of the linear portion of the arm 12 is oriented about 40 to 50 degrees, about 40 to 45 degrees, or about 45 to 50 degrees, relative to the longitudinal axis A of the first aperture 15.

Referring to FIGS. 2 and 5, the arm 12 includes a recess or a third aperture 20 about its distal end 21. The third aperture 20 is preferably configured as a counterbore recess 22 having a cylindrical internal wall 24 with threads 26 for engaging the first adapter threads 112 on the adapter 100. In accordance with an aspect of the exemplary embodiment, the longitudinal axis C of the recess 22 is oriented about 40 to 50 degrees, about 40 to 45 degrees, or about 45 to 50 degrees, relative to the longitudinal axis A of the first aperture 15.

Figure 3:
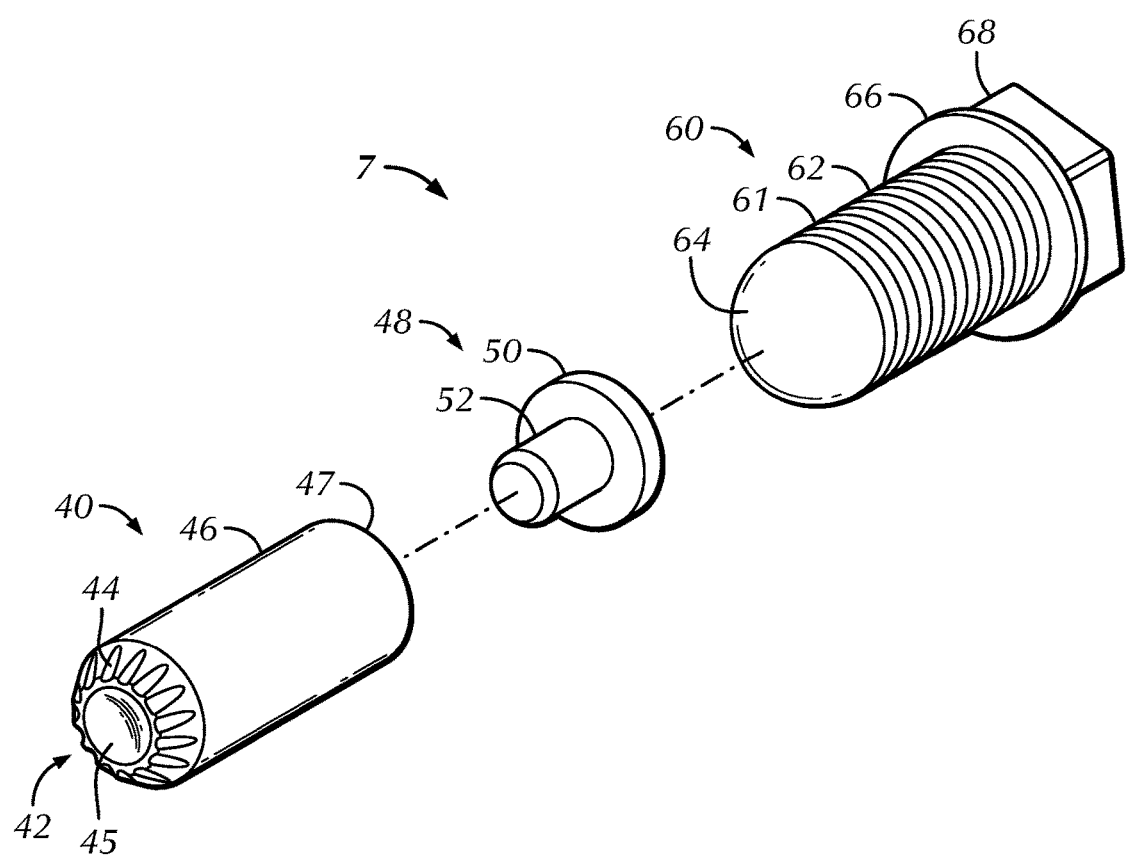
FIG. 3 is an exploded perspective view of an exemplary embodiment of a fastener applicable to the implant extraction device of FIG. 1.

As illustrated in FIG. 3, clamp shaft 40 is shaped to fit in cavity 18 through the second aperture 16. The body of clamp shaft 40 includes shaft member 46, while the proximal end of the shaft member includes a recess 47 configured to receive a bushing 48. The distal end of the shaft member 46 forms a rounded end, i.e., cup point 42. The cup point 42 is conically shaped with a plurality of ribs 44 and a concave surface 45 that is distally facing. The cup point engages a neck or portion of the implant received within the aperture 15.

The bushing 48 includes a cap section 50 having an indentation, and a pin section 52. The pin section 52 fits into the recess 47 in the shaft member 46. The cap section 50 has a diameter larger than the diameter of the pin section 52. Preferably, the cap section 50 is configured as a radially outwardly extending circular flange, but may be any shaped flange suitable for its intended purpose. Generally, the bushing 48 is preferably composed of a polymer, rubber, plastic or other synthetic material that is elastically deformable when contacted by the screw 60.

The screw 60 comprises a body 61 with screw threads 62 disposed on the exterior surface of the body 61. The screw 60 further includes a convex distal end 64. The screw 60 also includes a plate 66 about its proximal end with a cap 68 to enable the screw to be readily tightened and loosened during use, whether by hand or with a surgical wrench or other tool.

In use, the fastener 7 engages the implant received within the aperture 15 and applies a securing force to the implant in a direction transverse to the longitudinal axis A of the aperture 15, or in a direction parallel to longitudinal axis B.

Figure 4:
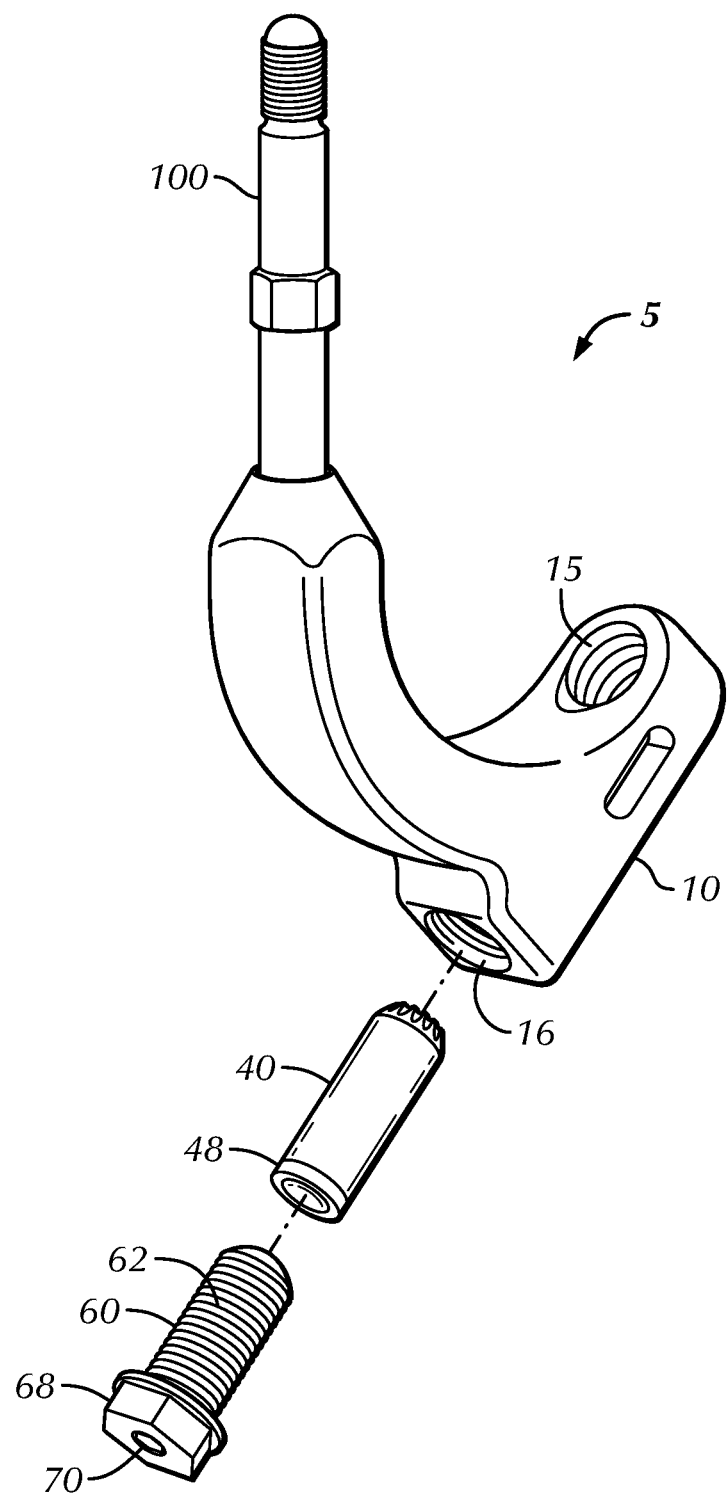
FIG. 4 is an exploded perspective view of the implant extraction device of FIG. 1.

As shown in FIGS. 3 and 4, the cap 68 is configured as a hexagonal bolt head, but other shapes may also be used as long as they provide a surface that can be gripped to tighten or loosen the screw. As shown in FIG. 4, the cap 68 also includes a cavity 70 having a hexagonal shape so as to be engageable with a hex wrench to facilitate tightening or loosening of the screw 60. The cavity 70 may alternatively be formed into other shapes, such as those found on the heads of standard slot screws, Phillips screws, or Robertson (square) screws. The cavity 70 can be formed as any shape that would allow engagement by standard or custom-designed tools. In operation, when the neck of a hip implant is inserted into the first aperture 15, the screw 60 is turned using a surgical tool adapted to fit the cap 68, thereby engaging the screw threads 62 with the cylindrical threads 19 so that the distal end 64 of the screw 60 contacts the bushing 48, compressing the elastic bushing to deliver compressive force through the clamp shaft 40 to engage the head, neck or other portion of the implant received within the aperture 15.

In accordance with another exemplary embodiment of the subject disclosure, there is provided a method of extracting a hip implant from a bone. The method includes the steps of attaching the implant extraction device 5 to a hip implant, orienting the terminal end of the arm to be substantially parallel with a longitudinal axis of a stem 1002 of the hip implant, and applying a force to the anterior hip extractor along an axis substantially parallel to the longitudinal axis D of the stem of the hip implant.

In sum, the anterior hip extractor utilizes a clamping shaft and a load screw that is positioned on the extractor so that they can be tightened with e.g., a T-handle or wrench that is accessed directly above an incision site. The clamping shaft has a ribbed cup point which provides clamping power as well as resistance to loosening due to vibration. The load screw presses against a plastic bushing which creates a crush zone which will compress when tightened and provide resistance to the load screw from backing out during extraction.

Advantageously, the anterior hip extractor is shaped so that e.g., the C-Frame sold by Shukla Medical can be attached to the extractor when it is attached to the implant. The geometry of the anterior hip extractor positions the C-Frame away from a patient's body so that a surgeon can work without being impeded by the patient's extremities. Once the C-Frame is attached to the anterior hip extractor, a mallet is then used to impact the C-Frame and transfer energy to the implant so it can be removed. The shape of the extractor is designed so that this energy is exerted parallel to the stem that is implanted into the patient's femur. This parallel force is necessary for energy efficient removal, as well as limiting the amount of stress created by perpendicular forces on the femur. The anterior hip extractor is designed to be specifically used in conjunction with the direct anterior approach. The clamp mechanism uses a clamping shaft and load screw to grip e.g., the trunnion of a hip implant. The clamping shaft is shaped so that the area contacting the implant is a cup point with ribs. This provides clamping power and resistance to vibration. The clamping shaft has a plastic bushing for the load screw to push into. This bushing will compress and provide a force to the load screw that resists backing out. The anterior hip extractor is designed to position the C-Frame away from the patient's body when clamped to the implant.

While the subject disclosure has been described with reference to exemplary embodiments, it will be appreciated by those skilled in the art that various changes may be made and equivalents may be substituted for elements thereof without departing from the scope of the subject disclosure. In addition, modifications may be made to adapt a particular situation or material to the teachings of the exemplary embodiments without departing from the essential scope thereof. It is to be understood, therefore, that the exemplary embodiments not be limited to the particular aspects disclosed, but it is intended to cover modifications within the spirit and scope of the subject disclosure as defined by the appended claims.

I claim:
1. An implant extraction device comprising:
  an arcuate frame that includes:
    a distal end having a recess for receiving an adapter, and
    a proximal end having:
      a first aperture for receiving an implant, the first aperture having a longitudinal axis that is oriented about 40 to 50 degrees relative to a longitudinal axis of the recess and
      a second aperture adjacent the first aperture for receiving a fastener.
2. The implant extraction device of claim 1, wherein the second aperture is in fluid communication with the first aperture.
3. The implant extraction device of claim 1, wherein the distal end comprises a linear portion.
4. An anterior hip extractor comprising:
  a base that includes:
    an aperture for receiving a hip implant, and
    a fastener for fastening the hip implant received within the aperture; and
  an arm arcuately extending from the base, wherein the arm includes:
    an arcuate portion having an arc length of about 40 to 60 degrees, and
    a linear portion extending from the arcuate portion, the linear portion having a longitudinal axis that is oriented about 40 to 50 degrees relative to a longitudinal axis of the aperture.
5. The anterior hip extractor of claim 4, wherein the base includes a cavity for receiving the fastener.
6. The anterior hip extractor of claim 5, wherein the cavity is in fluid communication with the aperture.
7. The anterior hip extractor of claim 4, wherein the fastener includes a screw and a clamp shaft.
8. The anterior hip extractor of claim 7, wherein the clamp shaft includes a plastic bushing.
9. The anterior hip extractor of claim 7, wherein the clamp shaft includes a rounded end having a plurality of ribs.
10. The anterior hip extractor of claim 4, further comprising an adapter attachable to the arm for attaching to a secondary extraction device.

11. The anterior hip extractor of claim 10, wherein the adapter is a substantially cylindrical shaft having threaded proximal and distal ends.

12. The anterior hip extractor of claim 10, wherein the adapter is threadedly engaged with the arm.

13. An anterior hip extractor comprising:
- a base that includes:
  - an aperture for receiving an implant, and
  - a fastener for fastening the implant received within the aperture; and
- an arm extending from the base and having a terminal end extending in a direction oriented about 40 to 50 degrees relative to a longitudinal axis of the base.

14. The anterior hip extractor of claim 13, wherein the base includes a cavity in fluid communication with the aperture for receiving the fastener.

15. The anterior hip extractor of claim 13, wherein the arm is arcuately extending from the base.

16. The anterior hip extractor of claim 13, wherein the fastener applies a securing force to the implant in a direction transverse to a longitudinal axis of the aperture.

17. A method of extracting a hip implant from a bone, comprising:
- attaching the anterior hip extractor of claim 13 to the hip implant;
- orienting the terminal end of the arm to be substantially parallel with a longitudinal axis of a stem of the hip implant; and
- applying a force to the anterior hip extractor along an axis substantially parallel to the longitudinal axis of the stem of the hip implant.

* * * * *